United States Patent [19]

Sato et al.

[11] Patent Number: 4,497,577
[45] Date of Patent: Feb. 5, 1985

[54] STEAM WETNESS MEASURING APPARATUS

[75] Inventors: Takeshi Sato, Hitachi; Syogo Tsuji, Katsuta; Kengo Shigeta, Hitachi; Akira Uenishi, Mito, all of Japan

[73] Assignee: Hitachi, Ltd., Tokyo, Japan

[21] Appl. No.: 383,186

[22] Filed: May 28, 1982

[30] Foreign Application Priority Data

Jun. 3, 1981 [JP] Japan ................................. 56-86242

[51] Int. Cl.³ ............................................ G01N 15/02
[52] U.S. Cl. ...................................... 356/336; 73/29; 250/227; 250/574; 356/339; 356/341; 356/342; 356/343
[58] Field of Search ................... 356/37, 72, 336, 338, 356/339, 341, 342, 343; 250/227, 573, 574; 73/29, 61.3; 374/42

[56] References Cited

U.S. PATENT DOCUMENTS 3,540,826  11/1970  Bisberg ................................. 356/338
4,137,462  1/1979   Wyler ............................. 250/227 X
4,154,529  5/1979   Dyott ............................. 356/342 X
4,295,368  10/1981  Jannone ........................... 73/61.3 X

OTHER PUBLICATIONS

Ferrara et al., "Evolution of the Fog Droplet Size Distribution Observed by Laser Scattering", *Applied Optics*, vol. 9, No. 11, pp. 2517-2521, 11/70.

Primary Examiner—David C. Nelms
Assistant Examiner—Matthew W. Koren
Attorney, Agent, or Firm—Antonelli, Terry & Wands

[57] ABSTRACT

A steam wetness measuring apparatus comprises a light source, a part defining a measuring space when the apparatus is inserted into a wet steam flow, an optical fiber bundle for transmitting the incident light beam from the light source to the measuring space, and optical fiber bundles for transmitting to a photo-electric converter element a plurality of scattered light beams of different scattering angles obtained by radiation of the incident light beam on the measuring space. The fact that the intensity of the scattered light beam changes with the wavelength of the incident light or changes with the scattering angle of the scattered light beam, in accordance with the particle size distribution of water droplets in the wet steam is used to determine the particles size distribution. The steam wetness is determined from the particles size distribution and the physical properties of the wet steam flow.

8 Claims, 11 Drawing Figures

STEAM WETNESS MEASURING APPARATUS

The present invention relates to an apparatus for measuring the moisture in a steam flow caused by a change of the state of the steam, namely, the steam wetness, in a device utilizing steam such as a steam turbine.

The moisture in the steam is present in the form of water droplets of a very small diameter ranging from less than 1 micron to several microns, and the number of the water droplet particles for each diameter is given as a certain kind of particle size distribution function. The steam containing such a moisture is called a wet steam. In equipments and devices using the steam, various inconveniences are caused as the wetness of the wet steam, namely, the mass concentration of the water droplets increases. In the case of a steam turbine, the turbine blade and the steam passage wall is corroded or eroded and the output power of the turbine is reduced. It is therefore a matter of importance to measure the wetness at various positions of the steam flowing in the turbine and to take an action to remove harmful phenomena while monitoring the condition of steam in connection with the turbine operating conditions.

As conventional methods of measuring the steam wetness are known a throttling calorimeter method in which the wet steam to be measured is sampled and reduced in pressure and a heat balance method in which the sampled wet steam is heated to evaporate the moisture and the wetness is calculated from the heat balance. These methods have such disadvantages that it is difficult to measure local wetnesses in the steam passage, and that the measurement takes a comparatively long time and hence it is impossible to measure the instantaneous wetness continuously. An article by J. S. Wyler, et al. entitled "Moisture Measurements in a Low Pressure Steam Turbine Using a Laser Light Scattering Probe" in Transaction of the ASME, Vol. 100, October 1976, p.p. 544 to 548, discloses a steam wetness measuring apparatus based on the principle of laser light attenuation. This measuring apparatus is so constructed that a photo signal of a beam of light passed through the wet steam to be measured is compared with a photo signal of a beam of light not passed through such a wet steam. This disclosed measuring apparatus fails to attain a superior accuracy of wetness measurement unless the Sauter mean diameter of water droplets is assumed to be a constant value of 0.3 $\mu$m or less, so that the accuracy of wetness measurement is greatly deteriorated for a wet steam involving Sauter mean diameter of larger than 0.3 $\mu$m. For example, the disclosed apparatus cannot substantially measure with a satisfactory occuracy the wetness of a wet steam involving Sauter mean diameter of 10 to 30 $\mu$m and having the wetness of the order of 5 to 15% which poses a problem in steam turbines.

An object of the present invention is to provide a steam wetness measuring apparatus capable of measuring the local wetness of a wet steam flow continuously and instantaneously and also capable of measuring the wetness over a wide range.

According to the present invention, an incident light beam transmitted by an optical fiber bundle is scattered by water droplets in a wet steam running in a measuring space of a detector section, the resulting scattered light beams are received by optical fiber bundles and applied to a photo-electric converter section, and signals delivered from the converter section based on the intensity of the scattered light beams are processed to determine the wetness of the steam.

Generally, the steam wetness, namely, the mass concentration of water droplets in a wet steam flow is equivalent to turbidity, and therefore the relation between the intensity of an incident light beam Jo and the intensity of a transmitted light beam or a scattered light beam J is given as $$(J/J_0) = e^{-\tau l} \tag{1}$$

where $\tau$ represents the turbidity and $l$ the length of the light path. If the intensity of the incident light beam Jo is assumed to be constant in this equation, it is possible to determine the turbidity equivalent to the steam wetness by detecting the intensity of the transmitted light beam or the scattered light beam. For the purpose of determining the steam wetness from the relation of equation (1), the steam wetness is required to change with the quantity of uniform water droplets of the same diameter. In an actual wet steam flow, however, a certain particle size distribution is formed for various droplet particle diameters according to the shape of the flow passage, the flow velocity, and the like. In a mesurement of a multidispersed particle system such as an actual wet steam flow where various sizes and quantities of droplets are distributed, therefore, it is necessary to determine the particle size distribution first and then to determine the mass concentration, namely, the wetness on the basis of the particle size distribution.

According to the present invention, the particle size distribution is determined from the intensity of scattered light beams and the result thereof is used to determine the steam wetness.

The above and other objects, features and advantages of the present invention will be made apparent by the detailed description taken in conjunction with the accompanying drawings, in which.

Figures 1A, 1B:
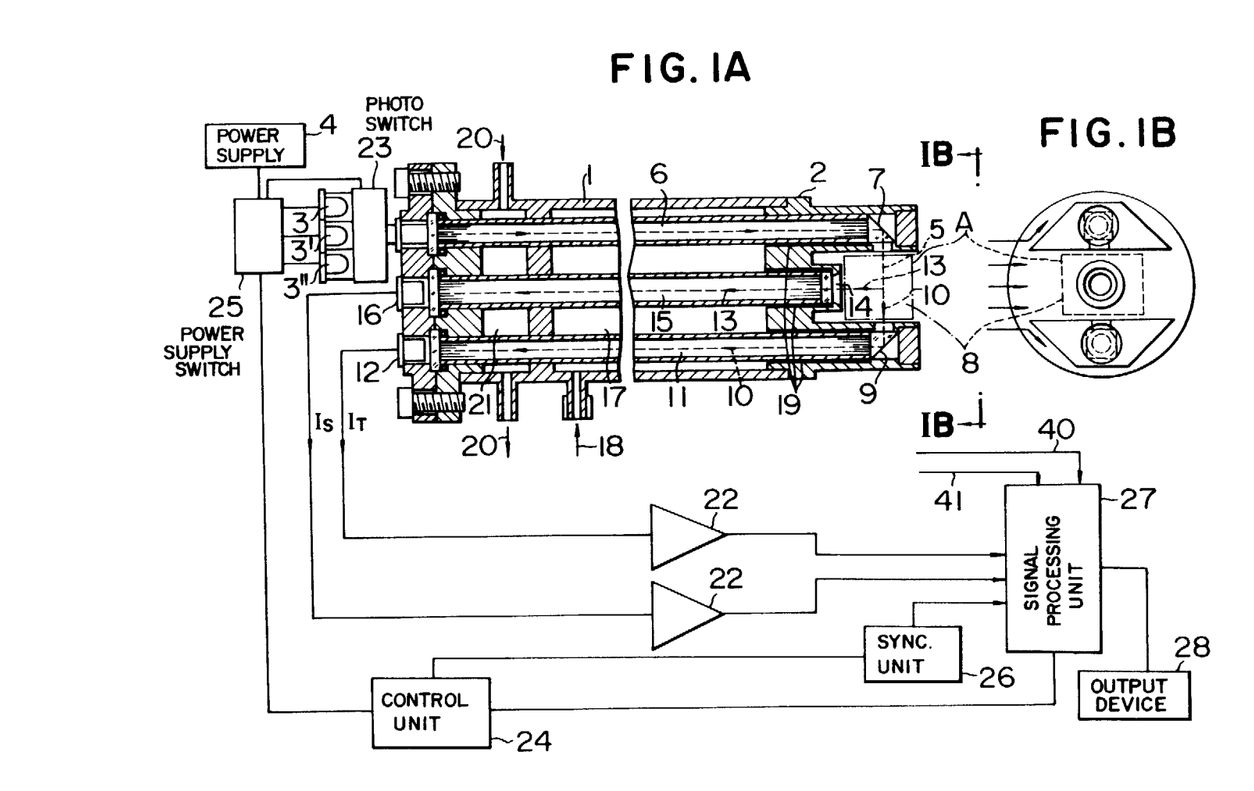
FIG. 1A shows a steam wetness measuring apparatus according to an embodiment of the present invention, in which a detector thereof is shown in sectional view and an electrical device is shown in a block diagram.
FIG. 1B shows the detector as viewed along the arrow IB in FIG. 1A.

A wetness measuring apparatus according to an embodiment of the present invention is shown in FIGS. 1A and 1B. A detector 1 of the wetness measuring apparatus is substantially cylindrical, and a forward end 2 (detection end) thereof is inserted into the steam flow to be measured and defines a measuring space A. The steam flows in the direction perpendicular to the sheet of FIG. 1A, that is, in the direction along arrows in FIG. 1B. The detector 1 contains therein an optical fiber bundle 6 for leading a light beam to be radiated on the measuring space A of the steam flow and optical fiber bundles 11 and 15 for leading light beams (scattered light beams) scattered by the water droplets in the steam to light-receiving elements 12 and 16 constructed by photo-electric conversion elements such as photodiodes. The forward end portion 2, contains a prism or a reflector 7 in contact with an end of the optical fiber bundle 6 for leading the light beam (incident light beam) from light sources 3, 3' and 3" through an optical switch 23 by means of the optical fiber bundle 6 and radiating this light beam on the measuring space A in a direction deflected by 90 degrees from the transmission path of the optical fiber bundle 6, and a prism or a reflector 9 at an end of the optical fiber bundle 11 for leading the light beam passed straight through the measuring space A, namely, the scattered light beam having the same direction as the incident light beam to the light receiving element 12. Further, the scattered light beam in a direction perpendicular to the incident light beam is led through a light-receiving window 14 and the optical fiber bundle 15 to the light-receiving element 16. Various scattered light beams may be considered as the scattered light beam in the direction perpendicular to the incident light beam, and a scattered light beam in the direction perpendicular to the sheet of FIG. 1 may be employed instead of the scattered light beam perpendicular to the incident light shown in the drawing, and the light-receiving window 14 and the optical fiber bundle 15 may be arranged accordingly. By the direction of the perpendicular scattered light beam employed, the measurement of the steam wetness is not affected. For simplying the construction, the scattered light beams in the plane perpendicular to the steam flow is preferably employed as shown in the drawing. In order to prevent water droplets from attaching to the surface of the light-receiving window 14, the reflectors or the prisms 7 and 9 in contact with the steam flow in the measuring space A for eliminating an adverse affection to the transmission of the incident light beam and the scattered light beams, a purge gas 18 is supplied into the hollow portion 17 of the detector 1 and, through grooves 19 formed in the inner surface of holes for insertion of the optical fiber bundles at the forward end portion 2, blown along the surfaces of the prisms or reflectors 7 and 9 and the light-receiving window 14. If the velocity of the purge gas blown to the prisms or reflectors 7 and 9 and the light-receiving window 14 is excessive, the wet steam flow in the measuring space A is disturbed thereby to make correct measurement of the wetness impossible. The pressure of the purge gas 18 is, therefore, adjusted properly in accordance with the pressure of the steam in the measuring space A.

In order to protect the light sources and the light-receiving elements from the heat of the steam flow, the cooling water 20 is supplied to the hollow portion 21.

The number of the light sources are not limited to three, but many light sources may be used each of which emits light of different single wavelength such as a light-emitting diode or laser diode. These light sources are illuminated sequentially by being supplied with a voltage from a power supply 4 through a power supply change-over switch 25 operated by a command signal from a control unit 24, so that the light beam of the light source illuminated is led to the optical fiber bundle 6 by the optical switch 23 actuated in synchronism with the change-over operation of the change-over switch 25. The light beam led by the optical fiber bundle 6 in this way provides the incident light beam 5 to the wet steam flow in the measuring space A. That light beam 13 scattered by the water droplets in the measuring space A which advances in the direction perpendicular to the incident light beam is led to the light-receiving element 16 such as a photo-diode by the optical fiber bundle 15, and converted into a voltage signal $I_S$. The scattered light beam 10 advancing in the same direction as the incident light beam 5, on the other hand, reaches the prism or reflector 9 and is led by the optical fiber bundle 11 to the light-receiving element 12 having the same characteristic as the light-receiving element 16 to be converted into a voltage signal $I_T$. The signals $I_T$ and $I_S$ thus obtained are amplified to a predetermined level by voltage amplifiers 22 and applied to a signal processing unit 27. The control unit 24 is for generating a power supply switching signal to be applied to the power supply change-over switch 25 in response to a command from the signal processing unit 27 and simultaneously supplying a synchronizing signal to the processing unit through a synchronizing unit 26. The processing unit 27 thus discriminates different wavelengths of the light beams from the light sources and stores in a memory thereof the signals $I_S$ and $I_T$ for each wavelength. An output device 28 is for visibly displaying the particle size distribution and the steam wetness obtained from the signal processing unit 27. Numerals 40 and 41 designate a temperature signal and a pressure signal respectively described later.

The steam wetness measuring apparatus according to this embodiment utilizes the dependency on the wavelength, of the intensity of the light beams scattered on the water droplets existing in the wet steam flow in the measuring space A or the fact that the intensity of the scattered light beams changes depending on the wavelength of the incident light beam in accordance with the particle size distribution of the water droplets. By analyzing the signals $I_T$ and $I_S$ every wavelength by the signal processing unit 27, it is possible to obtain the particle size distribution of the water droplets. The signal processing unit 27 includes a generally used electronic computer capable of storing a software function for determining the particle size distribution by analyzing the signals and computing the steam wetness from the particle size distribution.

Figure 2:
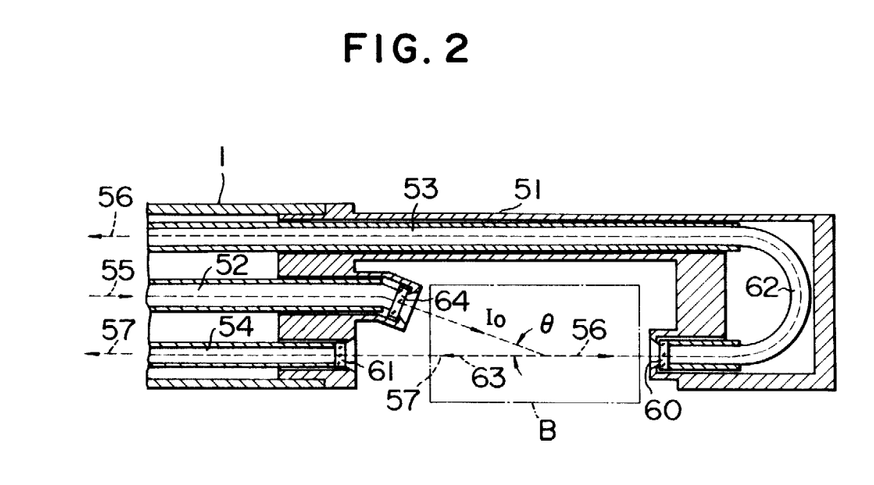
FIG. 2 is a sectional view of the essential parts of the detector of the steam wetness measuring apparatus according to another embodiment of the present invention.

Another embodiment of the present invention will be described with reference to FIG. 2. This embodiment includes a modification of the construction of the optical fiber bundles for the incident light beam 5, the scattered light beams 10 and 13 and the construction of the forward end portion 2 in the steam wetness measuring apparatus of FIG. 1, and the light-receiving element 16 is interchanged accordingly in position with the light sources 3, 3' and 3" and the optical switch 23 in FIG. 1., the other constructions and functions being exactly the same as those of the embodiment of FIG. 1. In the embodiment under consideration, an optical fiber bundle 52 for leading the incident light beam 55 is placed at the central portion of the cylindrical body of the detector 1, an optical fiber bundle 53 for leading the scattered light beam 56 to the light-receiving element and an optical fiber bundle 54 for leading the scattered light beam 57 to the light-receiving element are arranged on both sides of the optical fiber bundle 52. At the forward end portion 51, the end face 60 of the optical fiber bundle 53 for leading the forward scattered light beam 56 is arranged in opposed relation with the end face 61 of the otical fiber bundle 54 for leading the backward scattered light beam 57, through the measuring space B, in order to detect the forward scattered light beam 56 and the backward scattered light beam 57 resulting from the incident light beam 55 entering the measuring space B and scattered by the water droplets in the space B (the wet steam flowing in the direction perpendicular to the sheet of FIG. 2). For this purpose, the optical fiber bundle 53 is turned into a U-shape designated at 62 in FIG. 2. The forward end of the optical fiber bundle 52 is inclined at an angle θ to the line 63 connecting the end faces 60 and 61 and hence the end face 64 of the fiber bundle 52 is inclined so that the incident light beam 55 enters the space B from the direction of angle θ to the line 63. Similarly to the embodiment described with reference to FIG. 1, the incident light beam 55 is obtained by light-emitting diodes or laser diodes emitting lights of different wavelengths which are sequentially switched, and the forward scattered light beam 56 and the backward scattered light beam 57 for each of the wavelengths of the incident light 55 are led to the light-receiving elements by the optical fiber bundles 53 and 54 respectively, with the result that signals $I_T$ and $I_S$ similar to those shown in FIG. 1A are obtained from the scattered light beam 56 and from the scattered light beam 57, respectively.

The angle θ has no relation with the measurement of the steam wetness and may be determined as desired in accordance with the desired shape of the forward end portion 51, namely, the measuring section. Also, scattered light beams of any direction may be employed. Assuming that the scattered light beams 10 and 13 in FIG. 1A correspond to the forward scattered light beam 56 and the backward scattered light beam 57 respectively, the embodiment of FIGS. 1A and 1B may be considered to be a specific form of the embodiment of FIG. 2 with a different configuration of the measuring section. In the case of desiring the form of the measuring section as shown in FIG. 2, the angle θ may be selected to 10° to 30°, for instance.

In order to determine the steam wetness from the particle size distribution, it is necessary to measure the pressure and temperature of the steam flow and to determine the specific gravities of the gas and the water droplets from the pressure and temperature. The construction for measuring the pressure and temperature of the steam flow will be explained in relation with the embodiment of FIGS. 1A and 1B.

Figures 3A, 3B:
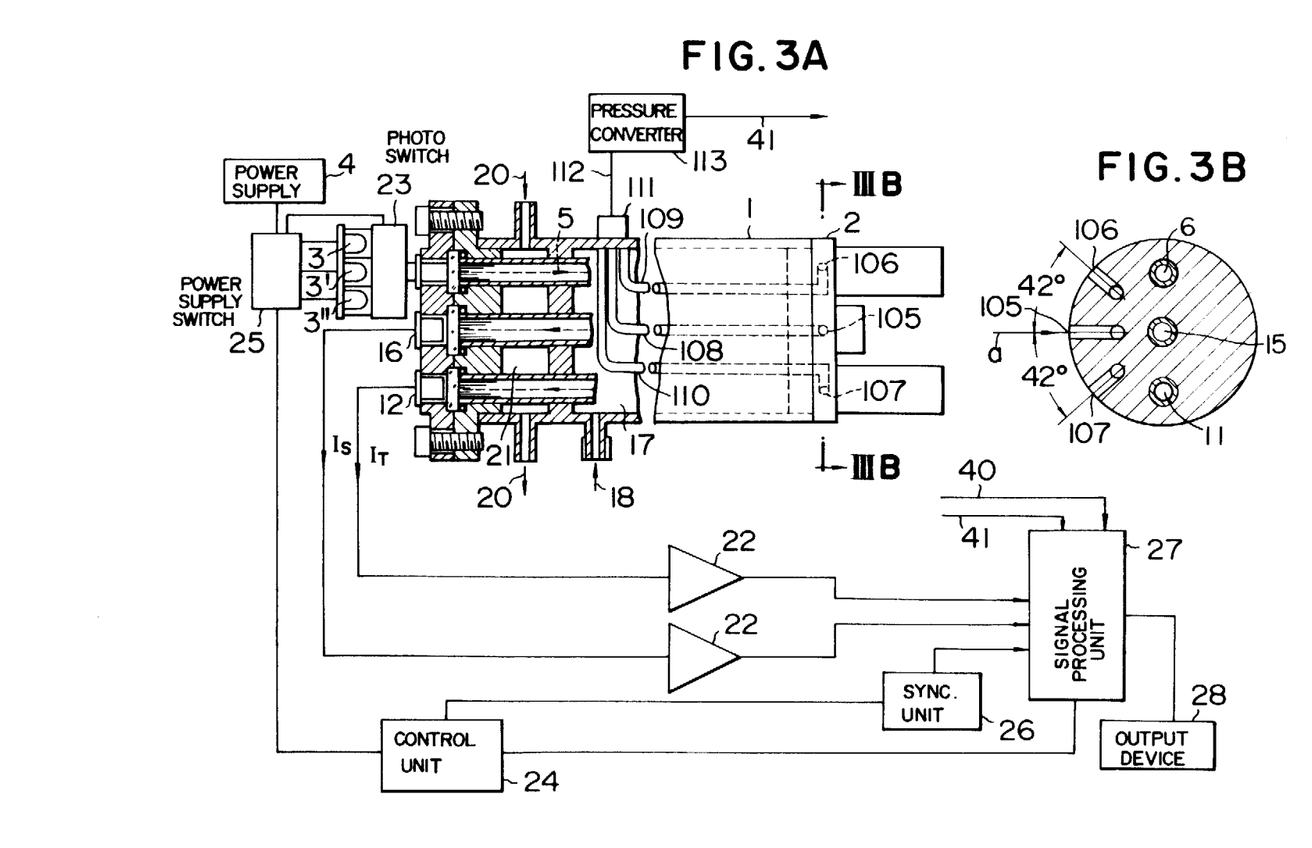
FIG. 3A is a diagram showing a construction for measuring the steam flow pressure in the embodiment of FIGs. 1A and 1B.
FIG. 3B is a sectional view taken along the line IIIB—IIIB in FIG. 3A.

A construction for measuring the pressure is shown in FIGS. 3A and 3B. Pressure measuring holes 105, 106 and 107 are provided on the outer periphery of the forward end portion 2 and communicate with pressure measuring tubes 108, 109 and 110 respectively which in turn connect to corresponding pressure detectors in a tube connector 111 through the hollow portion 17 of the detector 1. The pressure detectors are for converting the pressure into an electrical signal in such a way that in response to a signal 112, the pressure converter 113 converts the relation between pressure and voltage into a digital data which is applied as the signal 41 to the signal processing unit 27. As shown in FIG. 3B, the pressure measuring holes 105, 106 and 107 are located in such relative positions that when the pressure measuring hole 105 is directly opposed to the direction a of the steam flow, the pressure measuring holes 106 and 107 are placed at an angle of 42 degrees to the pressure measuring hole 105 on the periphery of the forward end portion 2. Three pressure measuring holes are provided for the reason that by balancing the pressures of the pressure measuring holes 106 and 107 with each other, the direction of the steam flow in the measuring space A can be crossed at right angle to the direction of radiation of the light beam on the one hand and as in the case of the pilot tube of cylindrical hole type used generally for measurement of fluid pressure, the pressure of the pressure measuring hole 105 provides a total pressure and those of the holes 106 and 107 a static pressure on the other hand.

Figures 4A, 4B:
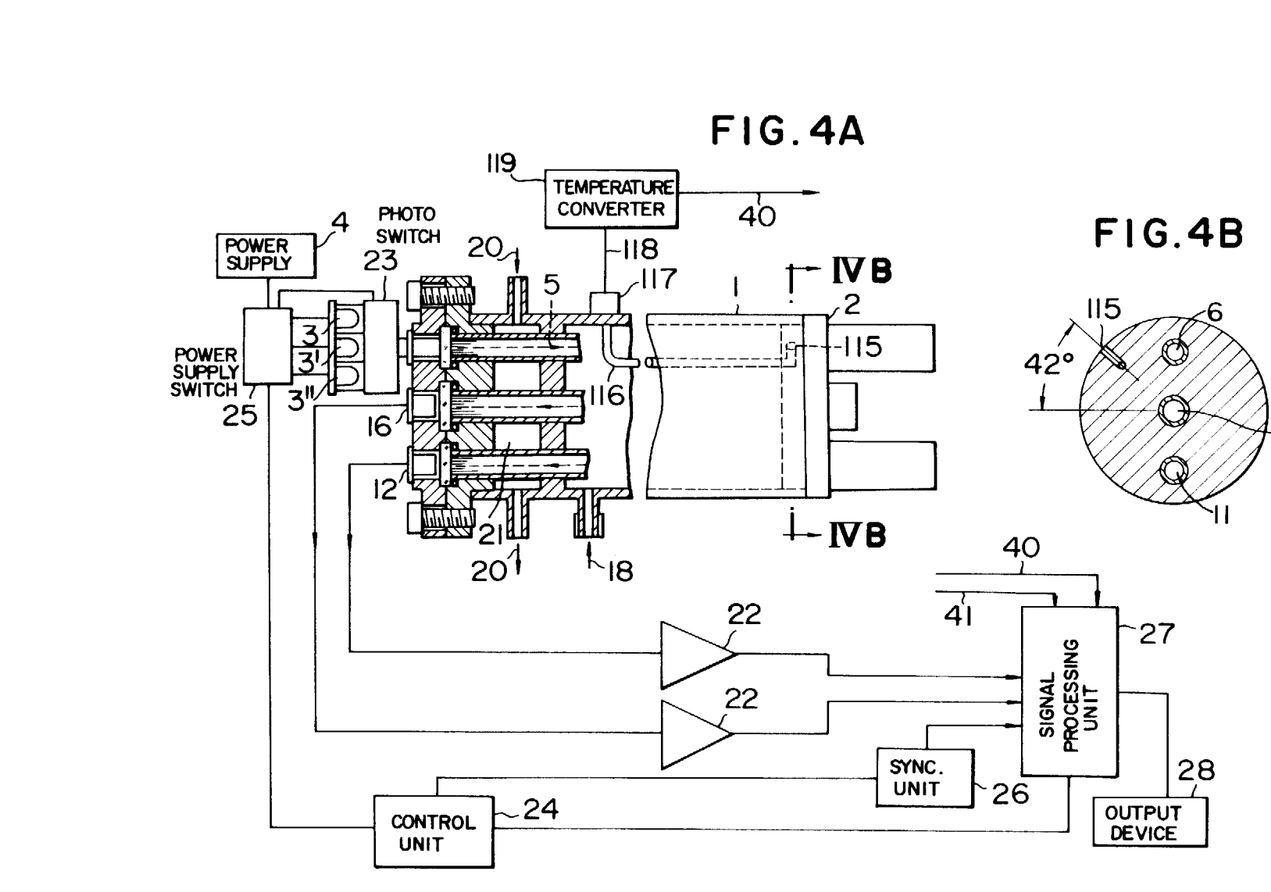
FIG. 4A is a diagram showing a construction for measuring the steam flow temperature in the embodiment of FIGS. 1A and 1B.
FIG. 4B is a sectional view taken along the line IVB—IVB in FIG. 4A.

A construction for temperature measurement is shown in FIGS. 4A and 4B. As in the case of pressure measurement, that part of the forward end portion 2 which is inserted into the cylinder of the detector 1 is provided with a hole 115 as shown in FIGS. 4A and 4B, and the forward end of a thermocouple 116 is inserted into the hole 115 from the hollow portion 17 of the detector 1 to such an extent as to almost reach the outer peripheral surface of the detector 1. The other end of the thermocouple 116 is connected to a thermocouple connector 117 in the detector 1. A voltage in the form of thermo electromotive force is measured by a temperature converter 119 as an outer signal 118, and after being digitally converted, the signal 40 is transmitted to the signal processing unit 27.

Now, explanation will be made of a method of processing the measured signals and computing the particle size distribution and steam wetness in relation with the embodiments of FIGS. 1A and 1B and FIG. 2.

This method is based on the fundamental formula $$I = \exp\left(-\frac{3}{2} \frac{\overline{K} \cdot C_v \cdot l}{D_{32}}\right) \quad (2)$$

where $$\overline{K} = \frac{\int_0^\infty K(\alpha, m_i) \cdot D^2 \cdot N(D) \cdot dD}{\int_0^\infty D^2 \cdot N(D) \cdot dD} \quad (3)$$

$$D_{32} = \frac{\int_0^\infty D^3 \cdot N(D) \cdot dD}{\int_0^\infty D^2 \cdot N(D) \cdot dD} \quad (4)$$

where I designates the intensity of a scttered light beam, $\overline{K}$ the scattering coefficient, $D_{32}$ Sauter mean diameter of water droplets, $\alpha = \pi D/\lambda$, D designates the diameter of water droplet, N(D) the particle size distribution function of water droplets, l the length of light path, $m_i$ the refractive index of water droplet, λ the light wavelength, and $C_v$ the volume concentration of water droplets. In this formula, let the wavelength of incident light beam be $\lambda_1$, $\lambda_2$ and $\lambda_3$, the scattering coefficients for the respective incident light beam wavelengths be $\bar{K}_1$, $\bar{K}_2$ and $\bar{K}_3$, and the intensity of the scattered light beam be $I(\lambda_1)$, $I(\lambda_2)$ and $I(\lambda_3)$. The relation shown below is obtained.

$$\left.\begin{array}{l}\dfrac{l_n[I(\lambda_1)]}{l_n[I(\lambda_2)]} = \dfrac{\bar{K}_1}{\bar{K}_2} = C_{12} \\[2ex] \dfrac{l_n[I(\lambda_2)]}{l_n[I(\lambda_3)]} = \dfrac{\bar{K}_2}{\bar{K}_3} = C_{23} \\[2ex] \dfrac{l_n[I(\lambda_3)]}{l_n[I(\lambda_1)]} = \dfrac{\bar{K}_3}{\bar{K}_1} = C_{31}\end{array}\right\} \quad (5)$$

The present invention uses the equations (2) and (5) above.

Figure 5:
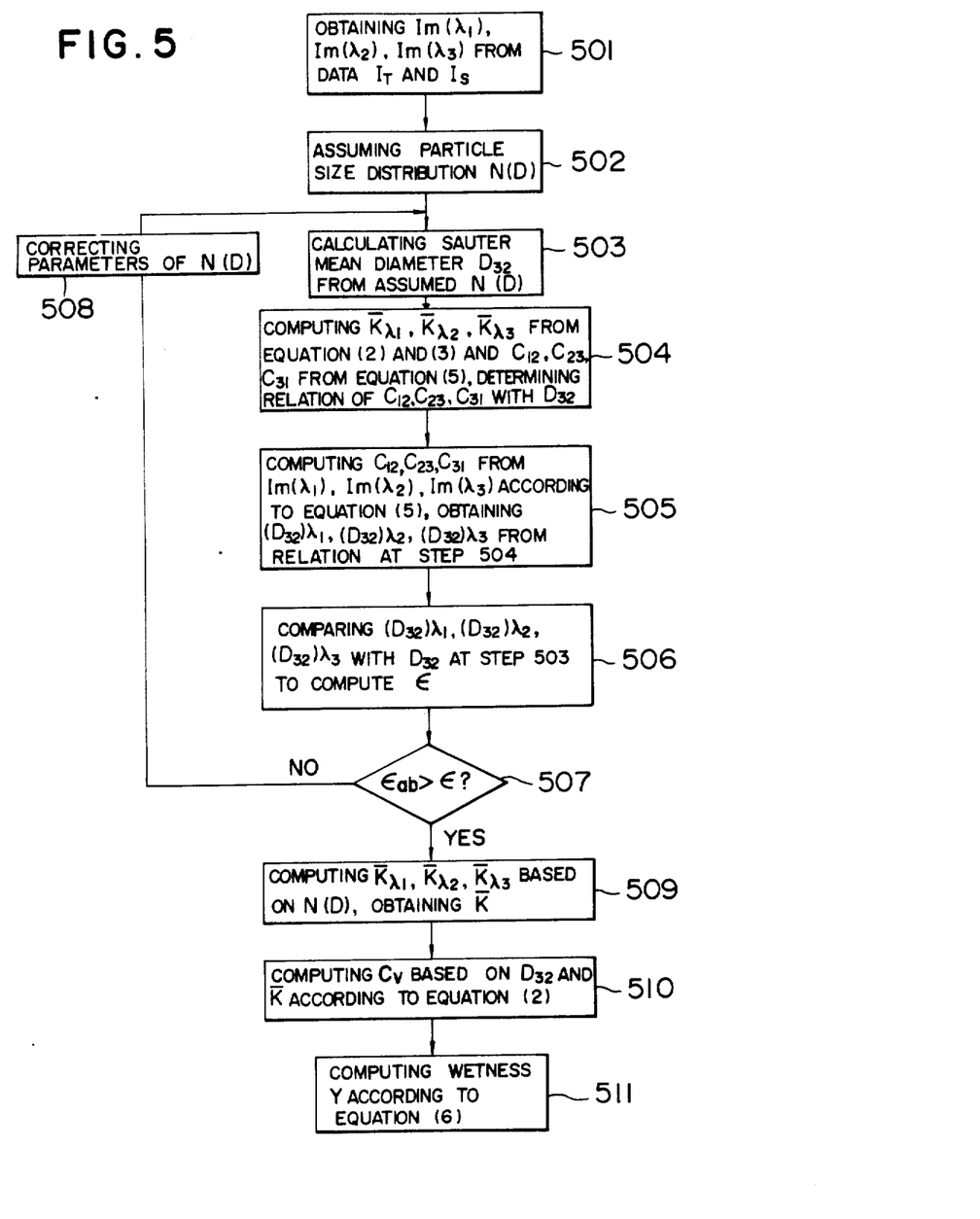
FIG. 5 is a flowchart for explaining a method of determining the steam wetness from the embodiments of FIGS. 1A and 1B and FIG. 2.

Now, an explanation will be made with reference to the flowchart of FIG. 5. At step 501, the forward scattered light intensity $I_T$ and the backward scattered light intensity $I_S$ corresponding to the respective incident light wavelengths $\lambda_1$, $\lambda_2$ and $\lambda_3$ are fetched as measurement data and ratios Im ($\lambda_1$), Im ($\lambda_2$) and Im ($\lambda_3$) between the forward scattered light intensity and the backward scattered light intensity are obtained for the respective wavelengths. At step 502, the particle size distribution function N(D) is assumed. N(D) takes various distribution forms including gamma distribution, logarithmic normal distribution and upper limit distribution, any one of which may be selected according to the manner of flow in the path where the moisture is to be measured. At step 503, the Sauter mean diameter $D_{32}$ is calculated from the assumed N(D). At step 504, $C_{12}$, $C_{23}$ and $C_{31}$ in equation (5) is computed in relation with equations (2) and (3) and the relation of $C_{12}$, $C_{23}$ and $C_{31}$ with $D_{32}$ is determined. At step 505, on the basis of the Im ($\lambda_1$), Im ($\lambda_2$) and Im ($\lambda_3$) obtained from the measurement data, $C_{12}$, $C_{23}$ and $C_{31}$ are computed according to equation (5) thereby to obtain Sauter mean diameters for respective wavelengths ($D_{32}$) $\lambda_1$, ($D_{32}$) $\lambda_2$ and ($D_{32}$) $\lambda_3$ on the basis of the relation determined at step 504. At step 506, $D_{32}$ obtained at step 503 is compared with ($D_{32}$) $\lambda_1$, ($D_{32}$) $\lambda_2$ and ($D_{32}$) $\lambda_3$ thereby to determine the probability error $\epsilon$ therebetween. At step 507, it is determined whether the probability error $\epsilon$ is within the tolerable error $\epsilon_{ab}$, and if $\epsilon_{ab} < \epsilon$, the process is passed to step 508, where the parameter of the particle size distribution function N(D) is corrected thereby to change the particle size distribution, followed by the repetitive execution of steps 503 to 507. As a result, if the relation $\epsilon_{ab} > \epsilon$ is obtained at step 507, the process proceeds to step 509. At step 509, $\bar{K}\lambda_1$, $\bar{K}\lambda_2$ and $\bar{K}\lambda_3$ are computed on the basis of the particle size distribution function N(D) thus determined, and the mean value $\bar{K}$ thereof are obtained. At step 510, the droplet volume concentration Cv is computed from equation (2) on the basis of $D_{32}$ and $\bar{K}$. At step 511, the specific gravity $\rho_f$ of the water droplet and the specific gravity $\rho_g$ of the gas are computed from the measurement data on pressure and temperature thereby to determine the wetness Y from the following equation:

$$Y = \dfrac{1}{1 + \left(\dfrac{1}{C_V}\right)(\rho_g/\rho_f)} \quad (6)$$

By taking the processes mentioned above, the particle size distribution N(D) and the wetness Y are determined.

Figure 6:
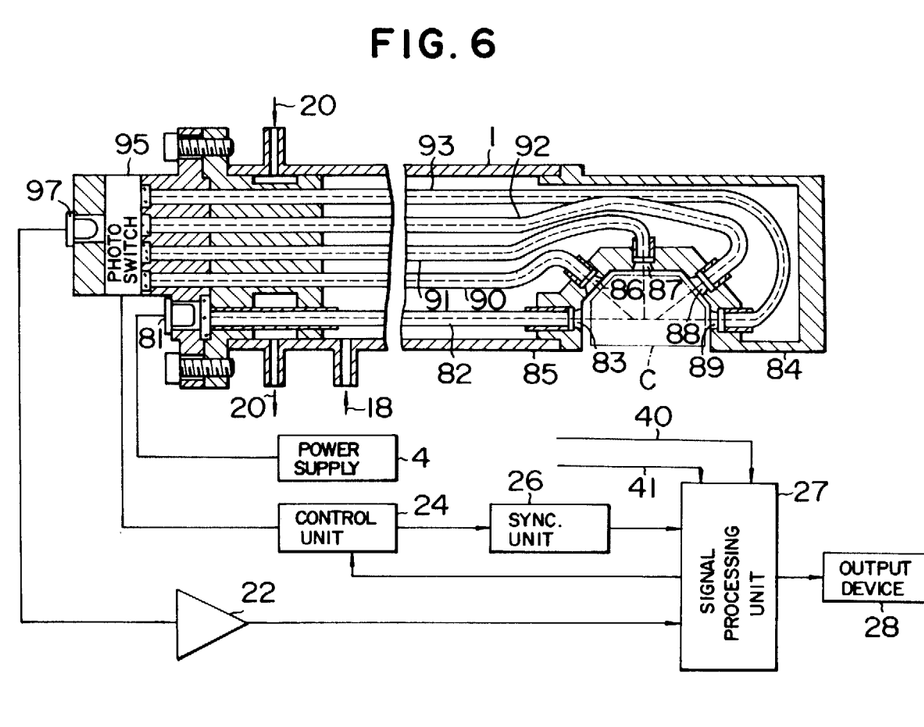
FIG. 6 is a diagram similar to FIG. 1A, showing a steam wetness measuring apparatus according to another embodiment of the present invention.
Figure 7:
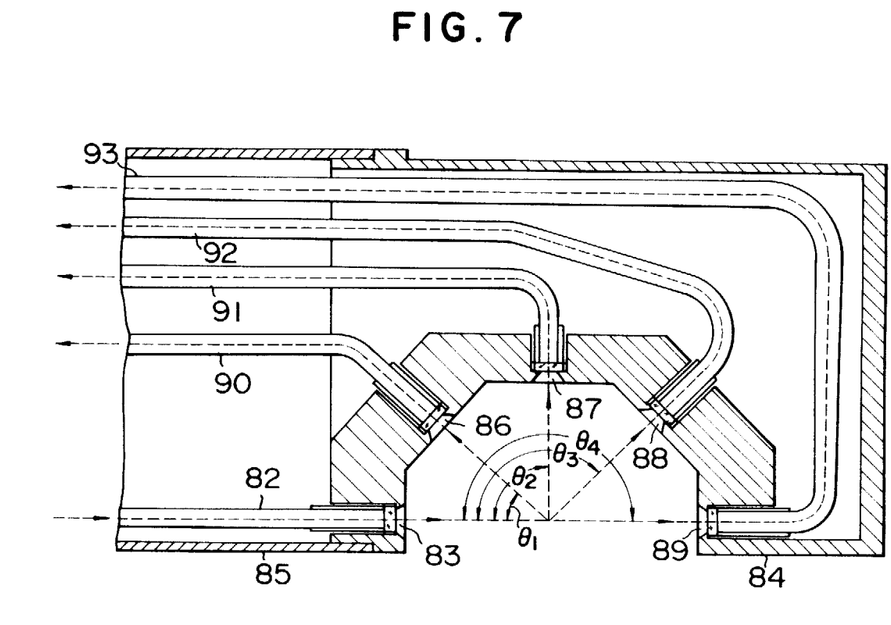
FIG. 7 shows the essential parts of FIG. 6 in enlarged form.

In the above-described embodiments, the fact that the intensity of the light beam scattered from the water droplets depends on the wavelength is utilized to compute the particle size distribution of the water droplets to determine the steam wetness. Since the intensity of the scattered light beam from the water droplets in the wet steam changes with the angle thereof with respect to the incident light beam, however, it is possible to calculate the particle size distribution by detecting the change of the intensity of the scattered light beams depending on the angle thereof with respect to the incident light beam, i.e. the detecting position of the scattered light beams, without changing the wavelength of the incident light beam. A stem wetness measuring apparatus utilizing such a dependency of the intensity of the scattered light beam on the scattering angle is shown in FIGS. 6 and 7 and will be described below. In FIG. 6, the same component elements as those shown in FIG. 1A are designated by the same reference numerals.

The apparatus shown in FIG. 6 comprises a single light-emitting diode or laser diode 81 energized by a power supply 4 for supplying incident light to the measuring space C. The light beam from the diode 81 is led to a radiation window 83 through an optical fiber bundle 82 arranged in the inner hollow portion of the cylindrical body 85 of the detector 1, thereby radiating the incident light beam into the measuring space C. In the space C, the wet steam containing water droplets flows in the direction perpendicular to the sheet of FIG. 6, so that the light beam radiated into the space C is scattered by the water droplets and the scattered light beams are received by a plurality of light-receiving windows 86, 87, 88 and 89 positioned at various angles to the direction of the incident light beam and provided on a surface contacted with the measuring space C formed in the forward end portion 84. The scattered light beams received at the light-receiving windows 86, 87, 88 and 89 have different intensities in accordance with the particle size distribution in the wet steam including water droplets, and the scattered light beams received at the respective light receiving windows are led to an optical switch 95 through optical fiber bundles 90, 91, 92 and 93 respectively connected with the light-receiving windows and arranged in the inner hollow portion of the cylindrical body 85. The control unit 24 generates a switch change-over signal in response to a command from the signal processing unit 27, and the optical switch 95 switches the light beams from the optical fiber bundles 90, 91, 92 and 93 at regular intervals of time in response to the switch change-over signal generated from the control unit 24. The light beam thus switched is led to a light-receiving element 97 which is similar to the light-receiving element 12 or 16 shown in FIG. 1A, whereby the light beam is converted into a voltage. The voltage from the light-receiving element 97 is amplified by the amplifier 22 and applied to the signal processing unit 27. The optical switch change-over signal from the control unit 24 is applied, on the other hand, to a synchronizing device 26, from which a synchronizing signal is applied to the signal processing unit 27, so that in synchronism with the operation of the optical switch 95, the signals from the light-receiving windows 86, 87, 88 and 89 which are converted into voltage at the light-receiving element 97 are stored in the memory of the signal processing unit 27 while classified every light receiving window. The purge gas 18 and the cooling water 20 are supplied in the same manner as in the embodiment of FIGS. 1A and 1B. Also, the construction for measuring the pressure and temperature of the steam flow is substantially the same as that explained with reference to FIGS. 3A and 3B, and the signal 41 representing the pressure and the signal 40 representing the temperature are applied to the signal processing unit 27.

The scattered light beam of any direction may be selected as desired. However, the angles $\theta_1$ to $\theta_4$ of the scattered light beams with respect to the direction of the incident light beam are required to be recognized. In view of the simplicity of the construction of the detection end and the recognition of the values of $\theta_1$ to $\theta_4$, however, it is preferable to use the scattered light beams in a plane perpendicular to the steam flow and containing the direction of the incident light beam. Further, it is preferable to use at least three scattered light beams, i.e. to provide at least three light-receiving windows.

In connection with the embodiment of FIGS. 6 and 7, a method of computing the particle size distribution and the steam wetness will be described. The intensity $I(\theta)$ of a scattered light beam at an angle of $\theta$ to the direction of the incident light beam is given as $$I(\theta) = \int_0^\infty A N(\alpha)[\sin^2(\alpha\theta)/\theta^2]d\alpha \tag{7}$$

where $\alpha = \pi D/\lambda$, A designates a constant, D the diameter of water droplet, $N(\alpha)$ is the particle size distribution function of water droplets. In the case where the wavelength $\lambda$ of the indicent light beam is constant as in this embodiment, the relation of equation (7) is expressed generally as $$I(\theta) = K \int_0^\infty i(\theta,D,m_l)N(D)dD \tag{8}$$

where $m_l$ designates the refractive index of the water droplet, and $i(\theta,D,m_l)$ designates Mie scattering function. In the range of the particle size distribution function $N(D)$, the range of the droplet diameter D is divided into n areas, and the intensity $I_k(\theta_M)$ of the scattered light beam for each area of D is computed from equation (8). $I_k(\theta_M)$ represents the intensity of the scattered light beam at an angle of $\theta_M$ for the value $D_k$ of the droplet diameter included in the k-th area of D. The relation between the measurements $I_m(\theta_1)$, $I_m(\theta_2)$, $I_m(\theta_3)$ and $I_m(\theta_4)$ of the intensity of the scattered light beams detected at the angles of $\theta_1$, $\theta_2$, $\theta_3$ and $\theta_4$ respectively shown in FIG. 7 with the value $I_k(\theta_M)$ is determined as follows.

$$I_m(\theta_M) = \sum_{k=1}^{n} C_k \cdot I_k(\theta_M) \tag{9}$$

where $I_m(\theta_M)$ is a general expression of $I_m(\theta_1)$, $I_m(\theta_2)$ and so on, M is the number of scattered light beams whose intensities are to be measured or the number of the angular postions of scattered light beams and $C_k$ is a factor determining the particle size distribution.

From equation (8), on the other hand, $I_m(\theta_M)$ is given as $$I_m(\theta_M) = K \int_0^\infty i(\theta,D,m_l) \sum_{k=1}^{n} C_k \cdot N_k(D) dD \tag{10}$$

where $N_k(D)$ is the particle size distribution in the k-th area of D.

Thus, the actual particle size distribution function N(D) is expressed as $$N(D) = \sum_{k=1}^{n} C_k \cdot N_k(D) \tag{11}$$

Since the droplet size distribution function N(D) is determined from equations (10) and (11), the steam wetness Y is computed from the equation below, in the same manner as described with reference to the embodiments of FIGS. 1A and 1B and FIG. 2.

$$Y = \frac{1}{1 + \left(\dfrac{1}{C_V}\right)(\rho_g/\rho_f)} \tag{12}$$

In this embodiment, as shown in FIGS. 6 and 7, scattered light beams of four different angles of $\theta_1$ to $\theta_4$ are employed, but the present invention is not limited to such number of scattered light beams. However, it is preferable to use at least three scattered light beams of different angles for optimization of $C_k$ described later.

Figure 8:
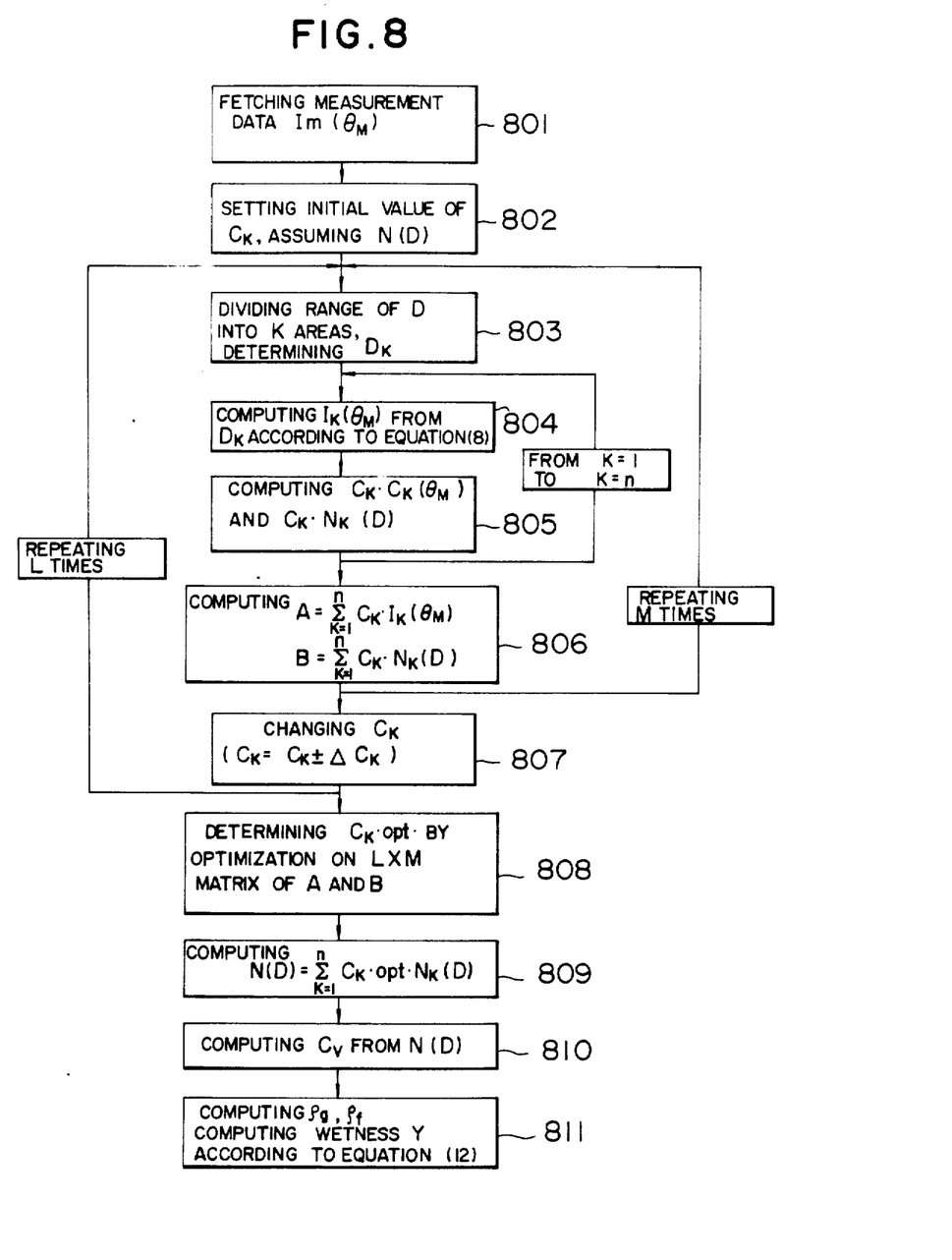
FIG. 8 is a flowchart for explaining a method of determining the steam wetness in the embodiment of FIG. 6.

Now, an explanation will be made with reference to the flowchart of FIG. 8. At step 801, the measurement data $I_m(\theta_M)$ is fetched. At step 802, the initial value of $C_k$ is set to provisionally determine the particle size distribution N(D). At step 803, the range of the water droplet diameter D is divided into n areas, and the value $D_k$ of the droplet diameter included in the k-th area of D is determined. At step 804, $I_k(\theta_M)$ is computed from equation (8) in the range of $D_k$. At step 805, $C_k \cdot I_k(\theta_M)$ in equation (9) and $C_k \cdot N_k(D)$ in equation (10) are computed. Steps 804 and 805 are executed repeatedly by the number n of divisions of D. At step 806, $$\sum_{k=1}^{n} C_k \cdot I_k(\theta_M) = A$$

in equation (9) and $$\sum_{k=1}^{n} C_k \cdot N_k(D) = B$$

in equation (10) are computed. Steps 803 to 806 are executed repeatedly by the number M of angular positions, with respect to the respective angular values of the scattered light beams. After that, at step 807, $C_k$ is changed by $\Delta C_k$. Steps 803 to 807 are repeated L times (in the order of several times). At step 808, the optimal value $C_{k,opt}$ of $C_k$ is determined by use of the optimization technique on the basis of an M×L matrix of the values A and B computed at step 806. At step 809, N(D) is computed from equation (11) using the value of $C_{k,opt}$. At step 810, the volume concentration Cv of the water droplet is computed from the value N(D) thus determined. At step 811, $\rho_f$ and $\rho_g$ are computed and, the steam wetness Y is computed according to equation (12).

As described above, according to the present invention, there is provided a steam wetness measuring apparatus for measuring the steam wetness from the relation between the wavelength of the incident light or the scattering angle of the scattered light beam and the intensity of the scattered light beam in accordance with the particle size distribution of water droplets when the light radiated on the water droplets in the steam flow is scattered. Comparison of the wetness measuring apparatus according to the present invention with the conventional wetness measuring apparatuses employing the throttling calorimeter method in which the wet steam to be measured is sampled and reduced in pressure or the heat balance method in which the sampled wet steam is heated to evaporate the moisture to compute the wetness from the heat balance, shows advantages of the wetness measuring apparatus according to the present invention as mentioned below. (1) A measuring space may be set in the wet steam flow and therefore no sampling is required. (2) The light beam is used as a medium capable of high-speed transmission without sampling, so that the wetness may be measured instantaneously without processing the steam such as reducing the pressure, or heating the wet steam. (3) Since a small measuring space is provided, the local wetness may be measured. In view of these advantages, the apparatus according to the present invention is widely applicable to measurement of the wetness distribution along the length of static blade and rotary blade of a steam turbine and the measurement of the wetness of the flow paths of a steam turbine. If the apparatus according to the invention is disposed at a specific position in the steam path of the steam turbine, it may be used also as a detector for monitoring the operating conditions of the steam turbine.

The wetness measuring apparatus according to the present invention is primarily intended to measure the wetness of the wet steam but may also be used for measuring the quantity of liquid contained in the form of droplets in a mixed fluid of gas and liquid.

What is claimed is:

1. A steam wetness measuring apparatus comprising:
   light source means;
   a portion defining a measuring space when said apparatus is inserted in a steam flow;
   photo-electric converter means;
   incident light beam transmitter means for transmitting an incident light beam from said light source means to said measuring space;
   scattered light beam transmitter means including a plurality of scattered light beam transmitting members for transmitting to said photo-electric converter means a plurality of scattered light beams of different scattering angles obtained by radiating the incident light beams on said measuring space;
   pressure detector means for detecting the pressure of the steam flow and producing an electrical signal associated with said pressure;
   temperature detector means for detecting the temperature of the steam flow and producing an electrical signal associated with the temperature; and
   processing means for computing the particle size distribution of water droplets in the steam flow on the basis of the electrical signals produced from said photo-electric converter means in accordance with the intensity of said scattered light beams and computing the steam wetness on the basis of said particle size distribution and said electrical signals produced from said pressure detector means and temperature detector means.

2. An apparatus according to claim 1, wherein said scattered light beam transmitter means includes two said scattered light beam transmitting members, said light source means includes light-emitting means for emitting a plurality of light beams of different wavelengths and change-over switch means for supplying the plurality of light beams sequentially to said incident light beam transmitter means, and said photo-electric converter means includes a plurality of photo-electric converter elements corresponding to said scattered light beam transmitting members respectively.

3. An apparatus according to claim 2, wherein said incident light beam transmitter means includes an optical fiber bundle for transmitting the incident light beam from said light source means to said measuring space and light path changing means for radiating the incident light beam on said measuring space in a predetermined direction,
   one of said scattered light beam transmitting members includes an optical fiber bundle for transmitting the scattered light beam of said predetermined direction and light path changing means for directing the scattered light beam of said predetermined direction to the light-receiving section of said optical fiber bundle, and
   the other of said scattered light beam transmitting members includes an optical fiber bundle having a light-receiving section for receiving the light beam scattered substantially perpendicularly to said predetermined direction and transmitting said perpendicularly scattered light beam.

4. An apparatus according to claim 2, wherein said incident light beam transmitter means includes an optical fiber bundle for transmitting the incident light beam from said light source means to said measuring space and radiating the incident light beam of said measuring space in a predetermined direction,
   one of said scattered light beam transmitting members includes an optical fiber bundle for receiving and transmitting the scattered light beam at a predetermined angle to said predetermined direction,
   the other of said scattered light beam transmitting members includes an optical fiber bundle for receiving and transmitting the scattered light beam in a direction opposite to the direction of said scattered light beam at the predetermined angle to said predetermined direction.

5. An apparatus according to claim 2, 3 or 4, further comprising control means for producing a control signal for controlling said light-emitting means and change-over switch means of said light source means in response to a command from said processing means, and synchronizing means for producing a synchronizing signal to said processing means in response to said control signal, said processing means being thereby capable of storing electrical signals corresponding to the intensities of said scattered light beams for respective wavelengths of the incident light beam.

6. An apparatus according to claim 1, wherein said scattered light transmitter means includes at least three said scattered light beam transmitting members for receiving at least three said scattered light beams of different angles to the direction of the incident light beam radiated on said measuring space by said incident light beam transmitter means.

said light source means includes light-emitting means for emitting a light beam of a predetermined wavelength, and said photo-electric converter means includes a photo-electric converter element for receiving the scattered light beams from said scattered light beam transmitting members, and change-over switch means for sequentially switching said scattered light beams to apply sequentially said scattered light beams to said photo-electric converter element.

7. An apparatus according to claim 6, wherein said incident light beam transmitter means includes an optical fiber bundle for transmitting the incident light beam from said light source means to said measuring space and radiating the incident light beam on said measuring space in a predetermined direction, and each of said scattered light beam transmitting members includes an optical fiber bundle for receiving and transmitting the scattered light beam at the corresponding one of said angles to said predetermined direction.

8. An apparatus according to claim 6 or 7, further comprising control means for producing a control signal for controlling the change-over switch means of said photo-electric conveter means in response to a command from said processing means, and synchronizing means for producing a synchronizing signal to said processing unit in response to said control signal, said processing unit thereby being capable of storing electrical signals corresponding to the intensities of said scattered light beams for respective angles of said scattered light beams.

* * * * *